US012708425B2

(12) United States Patent
Janich et al.

(10) Patent No.: US 12,708,425 B2
(45) Date of Patent: Aug. 18, 2026

(54) ELECTROSURGICAL GENERATOR WITH IMPROVED INVERTER CONTROL AND METHOD OF OPERATING

(71) Applicant: OLYMPUS WINTER & IBE GMBH, Hamburg (DE)

(72) Inventors: Fabian Janich, Potsdam (DE); Jelle Dijkstra, Berlin (DE); Raphael Behrendt, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 361 days.

(21) Appl. No.: 18/215,503

(22) Filed: Jun. 28, 2023

(65) Prior Publication Data

US 2024/0000494 A1 Jan. 4, 2024

Related U.S. Application Data

(60) Provisional application No. 63/356,631, filed on Jun. 29, 2022.

(51) Int. Cl.
*A61B 18/12* (2006.01)
*H02M 7/539* (2006.01)

(52) U.S. Cl.
CPC ......... *A61B 18/1206* (2013.01); *H02M 7/539* (2013.01); *A61B 2018/126* (2013.01);
(Continued)

(58) Field of Classification Search
CPC ........ A61B 18/1206; A61B 2018/1273; A61B 2018/128; A61B 2018/1286; H02M 7/539
See application file for complete search history.

(56) References Cited

U.S. PATENT DOCUMENTS

2017/0000549 A1 1/2017 Gilbert et al.
2017/0209202 A1* 7/2017 Friedrichs ............. A61B 18/14
(Continued)

FOREIGN PATENT DOCUMENTS

EP 3 248 560 A1 11/2017
EP 4 140 426 A1 3/2023
(Continued)

OTHER PUBLICATIONS

Zhao, C. et al., "A Single-Phase Dual Frequency Inverter Based on Multi-Frequency Selective Harmonic Elimination," IEEE, 2016, pp. 3577-3584.
(Continued)

*Primary Examiner* — Sean W Collins
(74) *Attorney, Agent, or Firm* — Oliff PLC

(57) ABSTRACT

Electrosurgical generator and method for outputting a high-frequency alternating voltage to an electrosurgical instrument, including an inverter that generates a high-frequency alternating voltage having variable frequency and amplitude which is fed to an output socket for the electrosurgical instrument. The inverter is a multi-level inverter controlled by a reference signal defining shape of the generated HF alternating voltage, the reference signal being defined by a datagram including a finite series of sequenced amplitude and frequency data vectors for a defined number of periods. By such datagrams including descriptive data for the desired HF sinusoidal curve, data amount and bandwidth required can be reduced. Thereby a variety of modes can be described using a minimum of data which can be as low as just a few dozen bytes long. This allows for efficient control even of complex modes.

18 Claims, 3 Drawing Sheets

| Data Field | Value | Bits |
|---|---|---|
| Polarity | 0 | 1 |
| nPeriods | 2 | 4 |
| amplitudeA0 | 127 | 7 |
| amplitudeB0 | 127 | 7 |
| amplitudeA1 | 0 | 7 |
| amplitudeB1 | 0 | 7 |
| frequencyA0 | 350 | 9 |
| FrequencyB0 | 350 | 9 |
| frequencyA1 | 19 | 9 |
| FrequencyB1 | 19 | 9 |
| | | 69 |

(52) U.S. Cl.
CPC . *A61B 2018/1273* (2013.01); *A61B 2018/128* (2013.01); *A61B 2018/1286* (2013.01)

(56) References Cited

U.S. PATENT DOCUMENTS

| | | | | |
|---|---|---|---|---|
| 2017/0312005 | A1 | 11/2017 | Friedrichs et al. | |
| 2021/0361340 | A1 | 11/2021 | Heckel et al. | |
| 2022/0069733 | A1 | 3/2022 | Bassi et al. | |
| 2022/0094278 | A1* | 3/2022 | Kraus | H02P 27/14 |
| 2023/0067224 | A1 | 3/2023 | Dijkstra et al. | |
| 2023/0069525 | A1 | 3/2023 | Dijkstra et al. | |

FOREIGN PATENT DOCUMENTS

| | | | |
|---|---|---|---|
| EP | 4 140 427 | A1 | 3/2023 |
| JP | H09-163755 | A | 6/1997 |
| JP | 2017-012752 | A | 1/2017 |
| WO | 2009/003959 | A2 | 1/2009 |

OTHER PUBLICATIONS

Translation of Mar. 24, 2023 Office Action issued in German Patent Application No. 102022116328.8.

* cited by examiner 12V
3-1
12V
3-2
12V
3-3
48V
3-4
48V
3-5
Vout 100
113
111
112
121
122
114
ST
+/-
n
$\binom{A}{f}$
$\binom{A}{f}$
F1
F2
SP
101
102

200
213
211
212
221
222
223
224
214
ST
+/-
n
$\binom{A}{f}$
$\binom{A}{f}$
$\binom{A}{f}$
$\binom{A}{f}$
F1
F2
F3
F4
SP
201
202
203
204

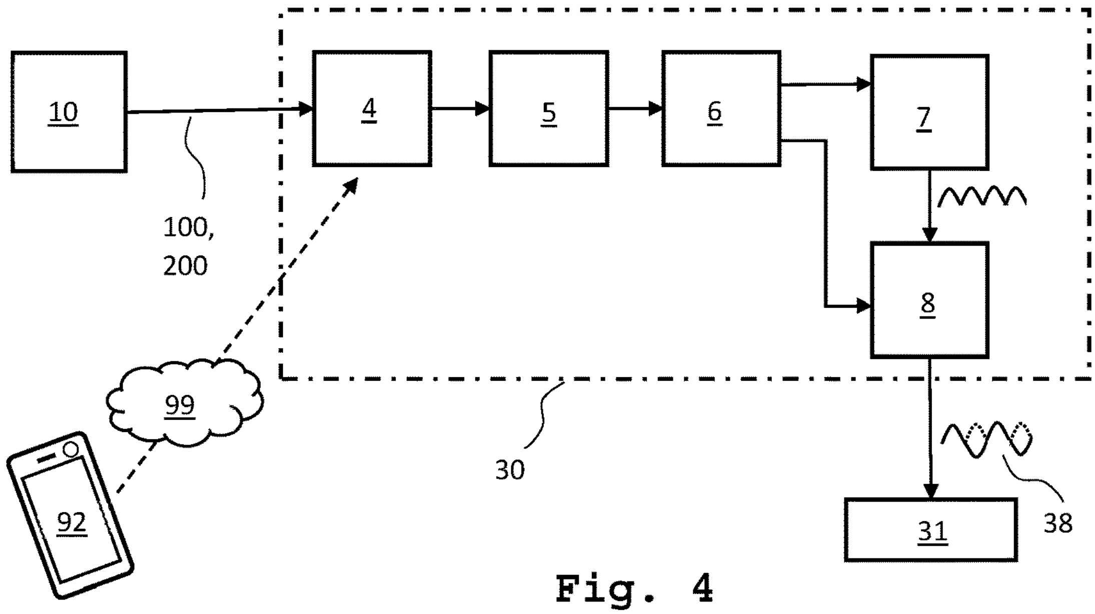
Fig. 4
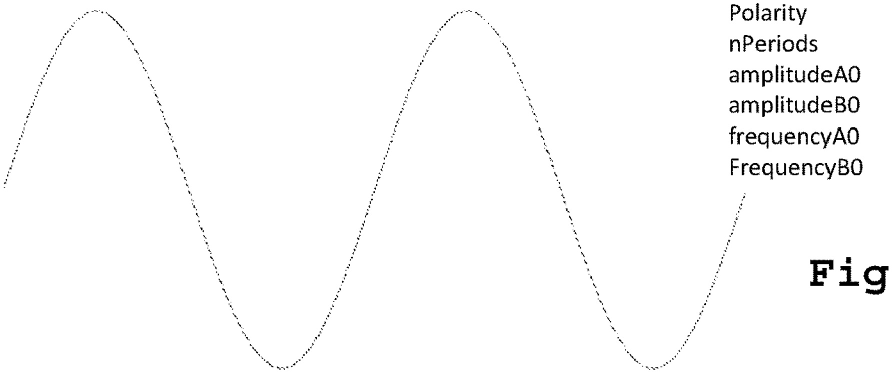
| Data Field | Value | Bits |
|---|---|---|
| Polarity | 0 | 1 |
| nPeriods | 1 | 4 |
| amplitudeA0 | 127 | 7 |
| amplitudeB0 | 127 | 7 |
| frequencyA0 | 350 | 9 |
| FrequencyB0 | 350 | 9 |
| | | 37 |
Fig. 5b
Fig. 5a
| Data Field | Value | Bits |
|---|---|---|
| Polarity | 0 | 1 |
| nPeriods | 2 | 4 |
| amplitudeA0 | 127 | 7 |
| amplitudeB0 | 127 | 7 |
| amplitudeA1 | 0 | 7 |
| amplitudeB1 | 0 | 7 |
| frequencyA0 | 350 | 9 |
| FrequencyB0 | 350 | 9 |
| frequencyA1 | 19 | 9 |
| FrequencyB1 | 19 | 9 |
| | | 69 |
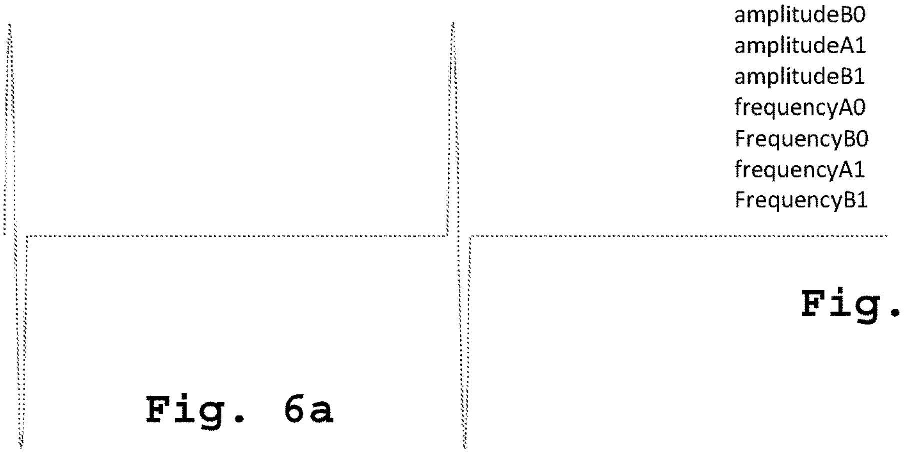
Fig. 6b
Fig. 6a

ELECTROSURGICAL GENERATOR WITH IMPROVED INVERTER CONTROL AND METHOD OF OPERATING

The invention relates to an electrosurgical generator designed to output a high-frequency alternating voltage to an electrosurgical instrument and a method of operating same. The electrosurgical generator comprises a control unit and an inverter for high voltage that generates a high-frequency alternating voltage having a variable frequency and amplitude which is fed to an output socket for connection of the electrosurgical instrument.

Electrosurgical generators typically feature a rather complex functionality comprising a large set of functions. Thereby, the surgical generators are enabled to cope with various applications. These functions differ in the way they provide power to the electrosurgical instrument. The different ways to supply the electrosurgical instrument with power are typically called "modes". If just cutting of tissue is to be accomplished, then a cutting mode is selected providing a medium voltage continuously to the electrosurgical instrument. If coagulation is more important, then a different mode is selected, e.g. a spray or coagulation mode which uses rather high voltage with a low duty cycle. There are many more different modes for other kinds of applications.

Presently, electrosurgical generators have high voltage generators mostly formed by means of resonance converters. This is a reliable and proven technology. However, it has drawbacks in that the frequency is not positively controllable and the amplitude can be adjusted only by changing the voltage of the DC supply of the resonance converters. Any changes of frequency and/or amplitude are rather unwieldy.

In order to improve adjustability, it is known to provide an electrosurgical generator with an inverter being configured as an H-bridge (EP 3 248 560 A1). However, in order to avoid formation of excessive harmonics special control schemes must be employed.

Further, electrosurgical generators comprising multi-level inverters in a cascaded topology have been developed by the present applicant. Thereby adjustability of the output signal could be considerably improved. Rapid changes of amplitude and frequency are possible. Further in principle random shapes of curvature for the output voltage are possible. However, doing so requires a dedicated high-performance controller, like an FPGA, that is enabled to drive the current valves of the inverter at a much higher frequency than the output frequency of the high voltage generated. Typical driving frequencies are 200 MHz for an output voltage alternating at a frequency of 400 kHz. This is doable, but providing the reference signal with such a high driving frequency requires a lot of data points in rapid succession, thereby demanding high-speed controllers which is costly.

It is an object of the invention to provide an electrosurgical generator and an improved inverter control that reduces said drawback.

The solution according to the invention resides in the features of the independent claims. Advantageous embodiments are the subject matter of the dependent claims.

In an electrosurgical generator designed to output a high-frequency alternating voltage to an electrosurgical instrument, comprising a control unit and an inverter for high voltage that generates a high-frequency alternating voltage having a variable frequency and amplitude which is fed to an output socket for connection of the electrosurgical instrument, according to the invention the inverter is a multi-level inverter controlled by a reference signal defining a shape of the generated high-frequency alternating voltage, the reference signal being defined by a datagram, the datagram comprising a finite series of sequenced amplitude and frequency data vectors for a defined number of periods.

First of all, a few terms shall be explained:

A multi-level inverter is an inverter being enabled to emit an output voltage at various levels, as opposed to providing on/off output only with positive and/or negative polarity. Typical topologies are, but not limited to, cascaded H-bridge, neutral clamped and flying capacitor.

A datagram is understood to be a data packet of a finite length. It is typically small sized to max. 256 Byte, particularly 50 Byte or less. It may optionally comprise source and destination identification but this not necessary.

The term "period" is used herein as denoting the time it takes to complete a full cycle of a waveform. Typically, this refers to the waveform of the high frequency AC voltage as generated by the inverter.

Controlling the inverter and providing its reference signal according to the present invention avoids the need for an expensive high-speed controller, like an FPGA. The invention provides a different approach for forming the reference signal, specifically forming it based on a datagram providing a flexible and concise description of the reference signal to be generated. To this end a special data format has been developed comprising a finite series of sequenced amplitude and frequency data vectors for a defined number of periods. The datagram describes the reference signal to be generated with a minimum of information.

Electrosurgical generators provide their high-frequency alternating output voltage in various modes. A simple mode is provided as a continuous oscillating voltage, e.g. for a "PureCut" mode. Further, there are several more complex modes, which are configured such that the output voltage is varying over time in terms of frequency, amplitude, duty cycle and/or crest factor. An example is a "SprayCoag" mode having a very high voltage in a spike like manner for a very short time, e.g. for one or two oscillations, followed by a much longer pause of very low or no voltage, wherein the duration of the pause is at least one dimension (10 times) longer than the spike, e.g. 20 times longer.

In order to be enabled to generate the output voltage according to rather complex modes, providing a reference signal for a multi-level inverter can be quite data intensive. A multilevel inverter generating a high-frequency alternating output voltage of up to 500 kHz is usually driven by a much higher frequency in the range of typically approximately 200 MHz. Depending on the number of levels a half, one or even two bytes may be required for each data point. This leads to a rather high bandwidth requirement which is demanding and costly.

The invention has realized that the amount of data and therefore the bandwidth required can be drastically reduced by providing a datagram comprising descriptive data for the desired high-frequency sinusoidal curve of the output voltage rather than a high-volume stream of data points. This is rather clear if the desired output voltage is a continuous voltage, wherein the datagram may just require a two digit number of bits. But surprisingly also more complex modes require just a small amount of data if the datagram according to the present invention is used, specifically the datagram comprising a finite series of sequenced amplitude and frequency data vectors for a defined number of periods. Thereby a variety of modes can be described using a minimum of data were which can be as low as just a few dozen bytes long. Clearly this is a drastic reduction of bandwidth requirements.

Preferably, the reference signal is to be formed by a reference signal forming unit. It is configured to form the reference signal as defined by the datagram. Further preferably, the reference signal forming unit comprises a receiver configured for receiving a data record describing the reference signal. Thereby, the reduced bandwidth requirement of the datagrams according to the present invention allows for an increased freedom concerning positioning the reference signal forming unit within the electrosurgical generator without being restricted to the vicinity of the source of the datagram.

The invention preferably allows for an efficient generation of the reference signal by using a synthesizer. To this end, the reference signal forming unit preferably comprises a decoder configured for decoding the data record received by the receiver and extracting the data vectors for each of the periods, a sequencer configured to output signals for amplitude and frequency from the extracted data vector for each period in a sequence as defined by the data fields, and to repeat this sequence; and a synthesizer configured to form for each of the data vectors an oscillation wave having the amplitude and frequency according to the respective data vector, wherein a series of the oscillation waves form the reference signal which is supplied to the inverter. In conjunction with being controlled by the datagrams according to the invention, continuous as well as non-continuous reference signals for the output voltage can be easily formed.

Preferably, the datagram comprises a plurality of data fields, one data field for each period, each data field comprising one of the data vectors having values indicative for amplitude and frequency of a respective one of the defined number of periods. Providing an own data field comprising the data vector for each of the periods allows for a high degree of flexibility in defining a complex sequence, thereby enabling the reference signal forming unit to form reference signals even for complex modes of the electrical surgical generator, such as modes having pulses of voltage separated by pauses.

Advantageously, the datagram further comprises a first additional data field indicative of a polarity, in particular polarity of a first half-wave of a first period. Thereby it can be selected whether the reference signal starts with a positive half-wave or with a negative half-wave, and thereby polarity (positive or negative first half-wave) of the high-voltage output voltage can be selected by the surgeon using the electrosurgical generator.

Further advantageously, the datagram further comprises a second additional data field indicative of the number of periods. By virtue of this the receiver and in particular the decoder and sequencer are enabled to check the datagram for completeness. Thereby, defective datagrams or datagrams missing data vectors for some periods could be easily identified and rejected, thereby improving operational safety.

Additionally or alternatively, the datagram may preferably comprise additional data fields indicative for start and stop information, in particular start and stop bytes. Thereby beginning and end of the datagram is clearly identified. This further improves data quality of the datagram. Using start and stop information, it is also possible to have datagrams with an unspecified number of periods, so that including additional periods with additional data vectors for more complex codes is facilitated. This improves the capability for future updates. Further, optionally the start and/or stop information may determine direction of data flow, thereby reading out the datagram data, and/or may comprise data integrity data fields, e.g. a checksum like a CRC (cyclic redundancy checksum).

Preferably, the datagram comprises at minimum data fields for two periods. Thereby a rather free selection of duty cycle is enabled which is a huge advantage for defining complex modes of the electrosurgical generator.

In a preferred embodiment, the synthesizer is configured to form half-wave oscillations, and the periods in the datagram relate to the duration of the half-wave oscillation. Thereby, for each half-wave an individual frequency and amplitude could be allocated. This allows for an even higher degree of granularity in defining the voltage curves of the modes. Further, it allows an asymmetric forming of the reference signal, thereby further increasing freedom in designing even more complex modes. It is worth to note that by virtue of the data vector concept the frequency and/or amplitude for the second half-wave can be different from the frequency and/or amplitude of the first half-wave. This is an important feature of the invention, and in particular the capability of having different frequencies for first and second half-wave is a huge benefit. Accordingly, the half-wave capability provides for greater flexibility in designing a huge variety of different reference signals for different modes.

Further, the synthesizer may be configured to form unipolar half-waves only, in particular positive half-waves. A synthesizer which is enabled to produce half-waves only can be simplified as opposed to a bipolar synthesizer. Further, for the same number of bits a higher quantization and therefore a better resolution with respect to the voltage amplitude can be achieved, thereby allowing a finer reproduction of sinusoidal voltage curves. As a further advantage, due to better quantization the amount of unwanted harmonics can be reduced.

Preferably, the synthesizer is coupled to an inversion circuit that is configured to invert every other half-wave emitted by the synthesizer. By inverting every second half-wave, a full bipolar oscillation can be formed employing the simplified half-wave synthesizer.

Preferably, the inversion circuit is a switchable inversion circuit being switchable according to a selection signal whether even or odd half-waves are to be inverted. Thereby it can be easily determined by the selection signal whether the reference signal and therefore the oscillation to be formed will start with a positive or a negative half-wave. Preferably the selection signal of the inversion circuit is automatically set according to a first additional data field indicative for polarity.

In particular if the electrosurgical generator supplying the output voltage to the electrosurgical instrument is operating for a longer time or for complex operation modes like those comprising an alternation of modes (e.g. altering between CUT and COAG mode), it may be necessary from time to time to update the data vectors of some, but not all, periods of the reference signal. Obviously, a new full datagram could be created and sent to be received and processed by the reference signal forming unit. However, it is even more efficient to not send the whole datagram, but only a reduced set (fragment). Advantageously, the receiver is further configured to receive a datagram fragment, the datagram fragment comprising a restricted number of the data fields with amended amplitude and frequency data vectors and an identifier for the period that is concerned, said restricted number being one or more but less than the defined number of periods. Thereby the reference signal forming unit is enabled to selectively replace amplitude and frequency data vector for one (or some) certain periods without requiring the full transmission of the whole datagram. This further reduces the amount of data to be transmitted. Further it allows for more rapid updates which is quite important for an ability to rapid alternate between operating modes, e.g. between CUT and COAG mode.

To this end, the decoder is preferably configured to extract the data vectors and identifiers, and the sequencer is configured to selectively replace for the period concerned the output signals for amplitude and frequency by those received in the decoded datagram fragment. Thereby only those data vectors that were actually altered need to be replaced, thereby simplifying and speeding up the procedure.

Advantageously, the datagram is condensed in that a bit length of amplitude and/or frequency value in the data vector is limited to the number of levels of the multi-level inverter and the frequency range, respectively. Thereby transmission of unnecessary longer data can be avoided, which leads to even more compact datagrams allowing faster transmission and processing.

Preferably, the datagram is less than 256 Bytes, preferably less than 50 Bytes.

In most cases the receiver is operationally coupled to the control unit for receiving the datagram, said control unit being local to the electrosurgical generator. However, in an advantageous embodiment it may also be possible that the receiver is configured to receive the datagram from a remote controlling unit. The compact datagram and the resulting reduced bandwidth requirement thus facilitate operation via a remote control connection, in particular a wireless connection.

The invention further relates to a corresponding method of operating the electrosurgical generator. For further explanation and to avoid unnecessary repetition, reference is made to the description of the electrosurgical generator as given above which is applicable mutatis mutandis.

The invention is explained in more detail below with reference to an advantageous exemplary embodiment. In the figures.

Figure 3A:
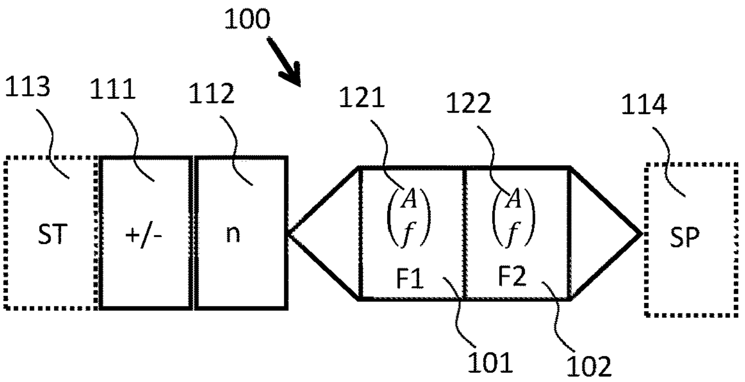
Figure 7:
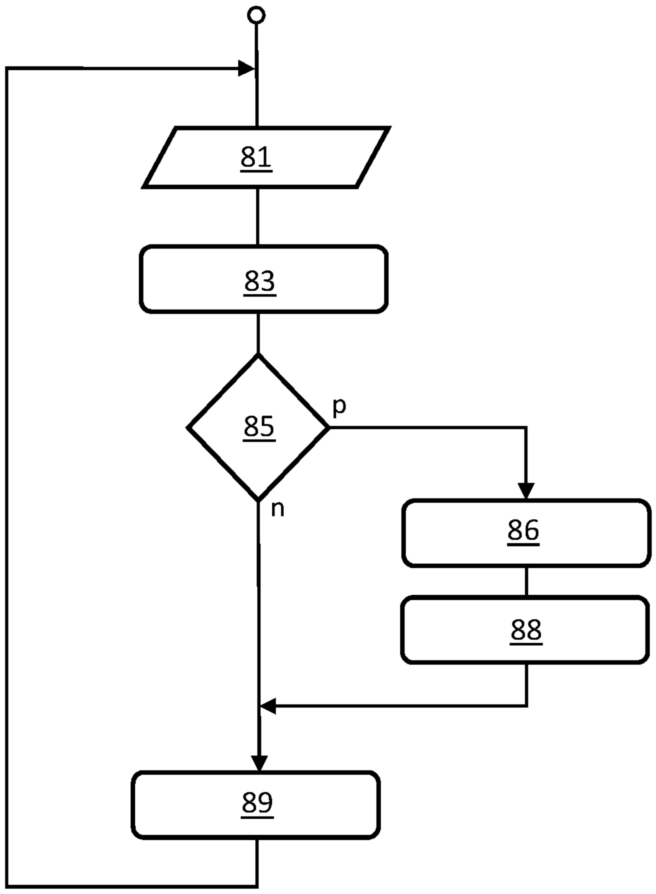

FIG. 3*a, b* shows a schematic view of two examples of datagrams;

FIG. 4 shows a block diagram of an exemplary embodiment of a reference signal forming unit;

FIG. 5*a, b* shows a first example for a reference signal and data of the corresponding datagram;

FIG. 6*a, b* shows a second example for a reference signal and data of the corresponding datagram; and FIG. 7 an exemplary flow diagram of a method for forming the reference signal.

Figure 1:
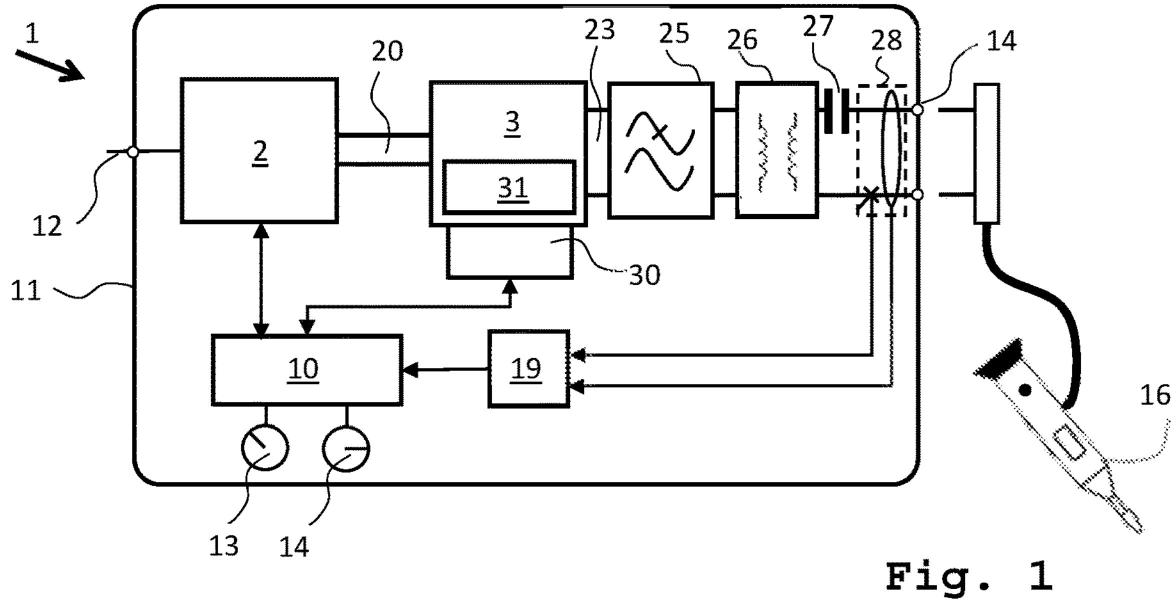
FIG. 1 shows a block diagram of a surgical generator according to an exemplary embodiment with an attached electrosurgical instrument.

An electrosurgical generator according to an exemplary embodiment is shown in a block diagram in FIG. 1. The electrosurgical generator being identified as a whole by reference numeral 1 comprises a housing 11 provided with an output socket 14 for an electrosurgical instrument 16. It is connected via a high-voltage connecting cable to the output socket 14 of the electrosurgical generator 1. A main connecting cable 12, which can be connected to a public electricity grid or other suitable means of electrical supply, is provided for the supply of electrical power to the electrosurgical generator 1.

The electrosurgical generator 1 comprises in the housing 11 a power supply unit 2 that is supplied with electrical power by the mains connecting cable 12 (see FIG. 1). The power supply unit 2 comprises a rectifier and feeds a DC link 20 with direct voltage, the DC link 20 supplying an inverter. The inverter 3 generates high-frequency alternating current in the high-voltage range of a few kilovolts. The high-frequency high voltage output is fed via an output line 23, low pass filter 25 and via an isolation transformer 26 stepping-up the high voltage to the output socket 14 comprising a series capacitor 27 for blocking off any DC current to the output socket 14. The electrosurgical instrument 16 can be plugged into the output socket 14. Output voltage and current at the output socket 14 are measured by a voltage and current sensor 28, and corresponding measurement signals are supplied to the control unit 10 by a feedback circuit 19. This is generally known in the art and will not be further explained for the sake of brevity.

Operation of the electrosurgical generator 1 is controlled by a control unit 10 which is connected to the power supply unit 2 and the inverter by means of signaling lines. The control unit 10 operates the electrosurgical generator 1 based on functions stored in a memory of the control unit 10. The functions define operating characteristics and modes of the electrosurgical generator 1. The functions can be selected by a user using input devices which can be conventional key and button interface and/or a touchscreen interface (not shown). For example, power to be outputted can be selected by a power selecting knob 13 and the mode to be employed can be selected by a mode selecting knob 14.

The inverter generates high-frequency alternating voltage in the range between 200 kHz and 4 MHz. The inverter is embodied as a multi-level inverter 3. Shape, frequency, duty cycle and amplitude of the voltage generated by the multi-level inverter are determined by an inverter control 31 based on a reference signal generated by a reference signal forming unit 30, which in turn is governed by the control unit 10 according to the power and mode as selected.

Figure 2:
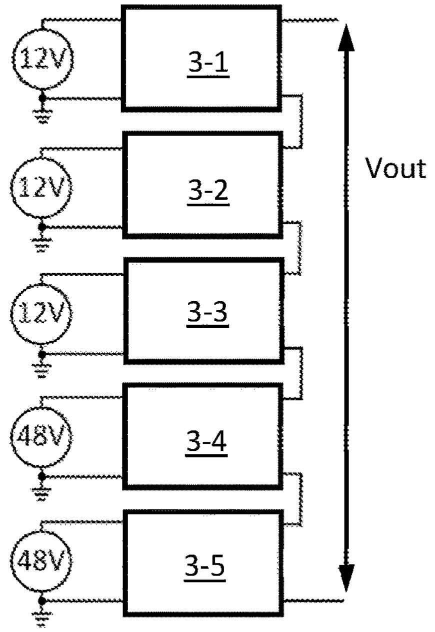
FIG. 2 shows a block diagram of a cascaded multi-level inverter.

The multi-level inverter 3 comprises a plurality of cells which are arranged in a cascaded formation as shown in FIG. 2. There are two different types of cells which are arranged in two groups which are groupwise supplied with different DC voltage. The first group comprises low-voltage cells 3-1, 3-2 and 3-3. They are supplied with a lower DC voltage, in the displayed embodiment 12 V. The second group comprises high-voltage cells 3-4, 3-5 which are supplied with a higher DC voltage, in the displayed embodiment 48 V. Both groups are connected in series so that the voltages outputted by each of the cells 3-1 to 3-5 are added to a common output voltage Vout. The configuration as shown can provide an output voltage ranging between −132 V and +132 V, which are equivalent to 23 levels in steps of 12 V.

In FIG. 3*a*) and b) examples for datagrams are shown. In the first example of the datagram shown in FIG. 3*a*) datagram 100 comprises data fields 101 and 102 for two periods. Each data field 101 and 102 comprises a data vector 121, 122, each having two values, one value "A" indicative for an amplitude and another value "f" indicative of a frequency of the respective period. So, these values describe the characteristics of the respective period in terms of amplitude and frequency. Further, the datagram 100 comprises a first additional data field 111 indicative of a polarity of the first period, i.e. whether the oscillation starts with a positive wave or a negative wave. Yet further, the datagram 100 comprises a second additional data field 112 indicative of a number "n" of periods for which data vectors are comprised in the data fields 101, 102, in the present instance "n" is 2.

Optionally, the datagram 100 may also comprise additional data fields 113, 114 for a start byte and stop byte, respectively.

The data fields available are shown in the following Table 1, for a datagram comprising data fields for up to 15 periods:

TABLE 1

| Parameter | Range | Bits | Description |
|---|---|---|---|
| Polarity | 0 or 1 | 1 | 0 - pos./1 - neg. |
| nPeriods | 1 . . . 15 | 4 | Number of Periods |
| amplitude0 | 0 . . . 127 | 7 | Rel. Ampl. 1st period |
| . . . | . . . | . . . | . . . |
| amplitude14 | 0 . . . 127 | 7 | Rel. Ampl. 15th period |
| frequency0 | 0 . . . 511 | 9 | Freq. of 1st period |
| . . . | . . . | . . . | . . . |
| Frequency14 | 0 . . . 511 | 9 | Freq. of 15th period |

The lines of the table which are written in italics refer to additional data fields. The other lines comprise the data vector comprising an amplitude value and a frequency value for each of the up to 15 periods. The amplitude value is a relative amplitude value, not an absolute one.

Figure 3B:
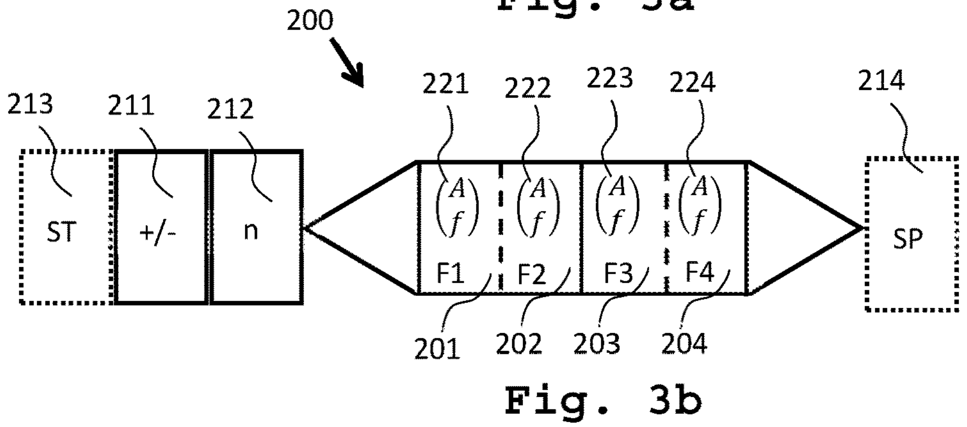

In FIG. 3*b*) a more complex datagram 200 is shown. It comprises four data fields 201, 202, 203 and 204 for two periods and separately for each half-wave of either period. Either one comprises one of the data vectors 221, 222, 223, 224. Thereby, for the same period its positive half-wave can have a different amplitude and/or frequency than its negative half-wave. Further, similar to the datagram 100, the datagram 200 also comprises an additional data field 211 for polarity and an additional data field 212 for the number of periods. The value in the additional data field 211 is indicative for the polarity of the first half-wave of each period. Further, the datagram 200 may also comprise optionally additional data fields 213, 214 for a start byte and stop byte, respectively.

The data fields for datagram 200 having data fields separately for each half wave are shown in the following Table 2:

TABLE 2

| Parameter | Range | Bits | Description |
|---|---|---|---|
| Polarity | 0 or 1 | 1 | 0 - pos./1 - neg. |
| nPeriods | 1 . . . 15 | 4 | Number of Periods |
| amplitudeA0 | 0 . . . 127 | 7 | Rel. Ampl. 1st period 1st half-wave |
| . . . | . . . | . . . | . . . |
| amplitudeA14 | 0 . . . 127 | 7 | Rel. Ampl. 15th period 1st half-wave |
| amplitudeB0 | 0 . . . 127 | 7 | Rel. Ampl. 1st period 2nd half-wave |
| . . . | . . . | . . . | . . . |
| amplitudeB14 | 0 . . . 127 | 7 | Rel. Ampl. 15th period 2nd half-wave |
| frequencyA0 | 0 . . . 511 | 9 | Freq. of 1st period 1st half-wave |
| . . . | . . . | . . . | . . . |
| FrequencyA14 | 0 . . . 511 | 9 | Freq. of 15th period 1st half-wave |
| frequencyB0 | 0 . . . 511 | 9 | Freq. of 1st period 2nd half-wave |
| . . . | | . . . | . . . |
| FrequencyB14 | 0 . . . 511 | 9 | Freq. of 15th period 2nd half-wave |

Similar to Table 1, the lines of Table 2 being written in italics refer to additional data fields. The other lines comprise the data vector comprising an amplitude value and a frequency value for either half-wave of each of the up to 15 periods. The amplitude value is a relative amplitude value, not an absolute one. It is worth to note that by virtue of these datagrams 200 the frequency of the second half-wave can be different from the frequency of the first half-wave. This is an important feature of the invention and provides for greater flexibility in designing a huge variety of different reference signals for different modes.

Shown in FIG. 4 is a block diagram of an exemplary embodiment of a reference signal forming unit 30 receiving these datagrams 100, 200 in order to form the reference signal for the inverter 3. It comprises a receiver 4 which is connected to the control unit 10. It is configured to receive the datagram 100, 200 describing the reference signal to be formed from the local control unit 10 of the electrosurgical generator 1.

Optionally, it may also be possible that such a datagram 100, 200 is sent from a remote device 92 by, preferably secured wireless connection 99, thereby allowing the remote control of the reference signal forming unit 30. The low bandwidth requirement of the datagrams 100, 200 are favorable for remote control which is typically bandwidth limited.

The receiver 4 conveys the received datagram 100, 200 to a decoder 5. The decoder 5 is configured to decode the datagram and to extract the data vectors 121, 122, 221, 222, 223, 224 from the various data fields and further the data from the additional data fields 111, 112, 113, 114, 211, 212, 213, 214. The decoder 5 supplies the extracted data to a sequencer 6 which is configured to bring the data extracted from the data vectors for each period in a proper sequence as defined by the data fields, and once reaching the end of the sequence to start over in order to repeat this sequence again and again. This is performed until a new datagram with new data is received, or a data fragment is received comprising an update for some of the data vectors, and then these updated data vectors replace the respective former ones, without interrupting the sequence. The data "A" on amplitude and "f" on frequency as extracted from the data vectors is supplied to a digitally controlled synthesizer 7 which forms a continuous oscillation comprising a sequence of waves, amplitude and frequency of each of the waves of said sequence being determined by the data extracted from the data vectors of the datagram. It is to be noted that in the embodiment depicted in FIG. 4 the digitally controlled synthesizer 7 is optionally configured such as to provide a stream of unipolar, in this case positive, half-waves only. This allows for a doubled resolution with the same number of bits.

For achieving the missing negative half-waves, a switchable inversion circuit 8 is provided. It is configured to perform an inversion of every other half-wave, thereby forming the missing negative half-waves. For controlling of the inversion circuit 8, a signal concerning the polarity extracted from additional data field 111, 211 is applied. If the extracted polarity data calls for a positive polarity, the first and every subsequent odd half-waves will not be inverted and the inversion will be performed on the second and every subsequent even half-wave, thereby creating full waves having a positive first half-wave. Conversely, if the extracted polarity data calls for a negative polarity, the inversion will be performed on the first and every subsequent odd half-wave, thereby creating full waves with negative first half-wave. By virtue of this, the formation of the full wave reference signal 38 is completed and it is outputted from the reference signal forming unit 30 and supplied to the inverter control 31 for processing by the multi-level inverter 3.

An example for a reference signal formed in this manner by the reference signal forming unit 30 is depicted in FIG. 5*a*. The reference signal is a non-complex one. In the present example, it is a sinusoidal wave suited for a "pure cut" mode of the electrosurgical generator 1. The data values and parameters employed for the various data fields of the datagram are shown in FIG. 5*b*. Further, a bit length for each of the data fields is shown. The total amount of data required for controlling the multi-level inverter 3 by defining the reference signal with the datagram is just 37 bits. This datagram needs to be transmitted only once and the reference signal forming unit 30 will produce a continuous reference signal with the shape, amplitude and frequency as defined by said datagram. This is in stark contrast to the high amount of data required for conventional control of the multi-level inverter 3.

An example for a more complex reference signal is depicted in FIG. 6*a*. This reference signal is more complex and comprises two periods for which half-waves are defined. It thus employs a datagram like the datagram 200 shown in FIG. 3*b*. The frequency of the first period is a rather high frequency (350 Hz) and the frequency of the second period is much lower (19 Hz). Together with a high amplitude for the first period and a low, to be precise zero, amplitude for the second period, a needle like reference signal with a duty cycle of about 5.5% is created, which is a reference signal well suited for a "spray and coagulation mode" of the electrosurgical generator 1. As this example shows, even complex reference signals having high duty cycles can be formed by employing a minimum of data, the present example just 69 bits. Again, this is in stark contrast to the high amount of data required for conventional control of the multi-level inverter 3.

In FIG. 7 an exemplary flow diagram for a method of forming the reference signal for controlling the multi-level inverter 3 is shown. Upon receiving a datagram 100 in step 81 a reference signal will be formed in step 83 as detailed above. In many instances the reference signal as defined by the datagram 100 will be used directly (via branch "n") for controlling the inverter 3 in step 89 to define shape, frequency and amplitude of the high-frequency alternating voltage generated by the multi-level inverter 3. However, if a check for reception of a data fragment in step 85 reveals that such a data fragment was received then the flow of operation will branch off (via branch "p") to performing in step 86 an extraction of data vectors that are contained in the data fields as comprised in said data fragment. Subsequently, the data vectors retrieved thereby will replace the corresponding previous data vectors and an updated reference signal will be formed in step 88. Eventually, in step 89 the multi-level inverter 3 will be controlled based on the reference signal, including any updates by the data fragments if applicable, to generate the high-frequency alternating voltage having shape, frequency and amplitude as defined by the datagrams 100 used for forming the reference signal.

The invention claimed is:

1. An electrosurgical generator configured to output a high-frequency alternating voltage to an electrosurgical instrument, comprising a control unit and an inverter for high voltage that generates a high-frequency alternating voltage having a variable frequency and amplitude which is fed to an output socket for connection of the electrosurgical instrument, wherein the inverter is a multi-level inverter controlled by a reference signal defining a shape of the generated high-frequency alternating voltage, the reference signal being defined by a datagram, the datagram comprising a finite series of sequenced amplitude and frequency data vectors for a defined number of periods.

2. An electrosurgical generator of claim 1, wherein the reference signal is provided by a reference signal forming unit.

3. An electrosurgical generator of claim 2, wherein the reference signal forming unit comprises a receiver configured for receiving a data record comprising the datagram, a decoder configured for decoding the data record received by the receiver and extracting the data vectors for each of the periods, a sequencer configured to output signals for amplitude and frequency from the extracted data vector for each period in a sequence as defined by the data fields, and to repeat this sequence; and a synthesizer configured to form for each of the data vectors an oscillation wave having the amplitude and frequency according to the respective data vector, wherein a series of the oscillation waves form the reference signal which is supplied to the inverter.

4. An electrosurgical generator according to claim 1, wherein the datagram comprises a plurality of data fields, one data field for each period, each data field comprising one of the data vectors having values indicative for amplitude and frequency of a respective one of the defined number of periods.

5. An electrosurgical generator according to claim 1, wherein the datagram further comprises a first additional data field indicative of a polarity.

6. An electrosurgical generator according to claim 1, wherein the datagram further comprises a second additional data field indicative of the number of periods.

7. An electrosurgical generator according to claim 1, wherein the datagram comprises additional data fields indicative for start and stop information.

8. An electrosurgical generator according to claim 3, wherein the synthesizer is configured to form half-wave oscillations, and the periods in the datagram relate to a duration of the half-wave oscillations.

9. An electrosurgical generator according to claim 8, wherein the synthesizer is configured to form unipolar half-waves only.

10. An electrosurgical generator according to claim 9, wherein an inversion circuit is coupled to the synthesizer and is configured to invert every other half-wave emitted by the synthesizer.

11. An electrosurgical generator according to claim 10, wherein the inversion circuit is a switchable inversion circuit being switchable according to a selection signal whether even or odd half-waves are to be inverted.

12. An electrosurgical generator according to claim 11, wherein the selection signal is automatically set according to a first additional data field indicative for polarity.

13. An electrosurgical generator according to claim 3, wherein the receiver is further configured to receive a datagram fragment, the datagram fragment comprising a restricted number of the data fields with amended amplitude and frequency data vectors and an identifier for the period that is concerned, said restricted number being one or more but less than the defined number of periods.

14. An electrosurgical generator according to claim 13, wherein the decoder is configured to extract the data vectors and identifiers, and the sequencer is configured to selectively replace for the period concerned the output signals for amplitude and frequency by those received in the decoded datagram fragment.

15. An electrosurgical generator according to claim 1, wherein the datagram is condensed in that bit length of amplitude and/or frequency value in the data vector is limited to the number of levels of the multi-level inverter and a frequency range, respectively.

16. An electrosurgical generator according to claim 3, wherein the receiver is coupled to the control unit for receiving the datagram and/or is configured to receive the datagram from a remote controlling unit.

17. A method of operating an electrosurgical generator configured to output a high-frequency alternating voltage to an electrosurgical instrument, comprising a control unit and an inverter for high voltage that generates a high-frequency alternating voltage having a variable frequency and amplitude which is fed to an output socket for connection of the electrosurgical instrument, the inverter being a multi-level inverter; the method comprising:

forming a reference signal according to a datagram, the datagram defining the reference signal comprising a finite series of sequenced amplitude and frequency data vectors for a defined number of periods; and controlling the multi-level inverter by the reference signal defining a shape of the generated high-frequency alternating voltage.

18. A method of operating an electrosurgical generator configured to output a high-frequency alternating voltage to an electrosurgical instrument, comprising a control unit and an inverter for high voltage that generates a high-frequency alternating voltage having a variable frequency and amplitude which is fed to an output socket for connection of the electrosurgical instrument, the inverter being a multi-level inverter; the method comprising:

forming a reference signal according to a datagram, the datagram defining the reference signal comprising a finite series of sequenced amplitude and frequency data vectors for a defined number of periods; and controlling the multi-level inverter by the reference signal defining a shape of the generated high-frequency alternating voltage, wherein the reference signal is provided by a reference signal forming unit.

* * * * *